(12) United States Patent
Willner et al.

(10) Patent No.: US 6,701,271 B2
(45) Date of Patent: Mar. 2, 2004

(54) METHOD AND APPARATUS FOR USING PHYSICAL CHARACTERISTIC DATA COLLECTED FROM TWO OR MORE SUBJECTS

(75) Inventors: Barry E. Willner, Briarcliff Manor, NY (US); Edith H. Stern, Yorktown Heights, NY (US); David P. Greene, Ossining, NY (US); Philip Shi-lung Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 22 days.

(21) Appl. No.: 09/859,827

(22) Filed: May 17, 2001

(65) Prior Publication Data
US 2002/0173928 A1 Nov. 21, 2002

(51) Int. Cl.$^7$ .............................. G06F 15/00; G01D 1/00
(52) U.S. Cl. ........................................ 702/127; 702/182
(58) Field of Search .......................... 702/81, 127, 128, 702/130, 136, 182, 186; 600/300, 301, 310, 481; 128/903, 870; 434/257–259; 723/9–10, 14, 16; 705/1, 80

(56) References Cited

U.S. PATENT DOCUMENTS

| | | | | |
|---|---|---|---|---|
| 4,907,973 A | * | 3/1990 | Hon ............................ | 434/262 |
| 5,233,520 A | * | 8/1993 | Kretsch et al. ............. | 600/300 |
| 5,542,420 A | * | 8/1996 | Goldman et al. ........... | 600/301 |
| 5,762,503 A | * | 6/1998 | Hoo et al. ................... | 434/237 |

OTHER PUBLICATIONS

Cristiane G. Lau, "Shear Madness has right mix of character, audience", http:/the–tech.mit.edc/V113/N45/madness.45a.txt.html, vol. 113, No. 45, 2 pages.*

* cited by examiner

Primary Examiner—Bryan Bui
(74) Attorney, Agent, or Firm—Buckley, Maschoff & Talwalker LLC; Stephen C. Kaufman

(57) ABSTRACT

A system, method, apparatus, and computer program code for using physical characteristic information obtained from two or more subjects to help evaluate subjects or to determine a course of action to take with the subjects includes receiving data indicative of one or more physical characteristics from two or more subjects, determining an evaluation of the data, and providing a notification to a device of the evaluation. A physical characteristic of a subject might be or include the subject's heart rate, blood pressure, blood sugar level, posture, temperature, respiration rate, facial response or position, weight, height, galvanic skin response, pheromone emission, brain wave pattern or rhythm, odor, motion, etc., or a change in any one or more of them.

41 Claims, 8 Drawing Sheets

| EVALUATION IDENTIFIER 502 | EVALUATION DESCRIPTION 504 | SENSOR IDENTIFIER 506 |
|---|---|---|
| E-0234 | INTEREST LEVEL DETERMINATION | S-123456 S-867454 |
| E-4629 | RESTLESSNESS DETERMINATION | S-387766 |

METHOD AND APPARATUS FOR USING PHYSICAL CHARACTERISTIC DATA COLLECTED FROM TWO OR MORE SUBJECTS

FIELD OF THE INVENTION

The present invention relates to a method and apparatus for using information obtained from two or more subjects and, more particularly, embodiments of the present invention relate to methods, apparatus, and computer program code for determining a course of action based on information regarding one or more physical characteristics of two or more subjects.

BACKGROUND OF THE INVENTION

There are many situations in which it might be desirable to have information regarding how a subject or a group of subjects feels about information being delivered or presented to them or how the subjects react while information is being delivered or presented to them. For example, a teacher may wish to know if the students in her class understand the material the teacher is discussing. A lecturer may wish to know what portions of his lecture the audience members find most interesting. Alternatively, the lecturer may want to have a better idea of when to take a break. An entertainer may wish to know what ending to provide to a story or song medley being presented to an audience.

While devices exist that allow take information from a single subject and provide information regarding the single subject, unfortunately, there is no way for an observer of two or more subjects to take objective measurements of the subjects and use the information to direct the observer or a device under the observer's control along one of several courses of action or to evaluate how best to alter or change what the observer or device is currently doing. It would be advantageous to provide a method and apparatus that overcame the drawbacks of the prior art. In particular, it would be desirable to use physical characteristic information obtained from or about two or more subjects and to determine a course of action based on such information or an evaluation of the information.

SUMMARY OF THE INVENTION

Embodiments of the present invention provide a system, method, apparatus, and computer program code for using physical characteristic information obtained from or about two or more subjects and, more particularly, embodiments of the present invention relate to methods, apparatus, and computer program code for determining a course of action based on the information or an evaluation of the information. Information or other data regarding physical characteristics of two or more subjects may be received from one or more sensors carried, worn, or handled by the subjects or otherwise associated with the subjects. The data may be indicative of a variety of physical characteristics. For example, a physical characteristic of a subject might be or include the subject's heart rate, blood pressure, blood sugar level, posture, temperature, respiration rate, facial response or position, weight, height, galvanic skin response, pheromone emission, brain wave pattern or rhythm, odor, motion, etc., or a change in any one or more of them.

Based on the data received regarding one or more physical characteristics, an evaluation of the data may be determined or a course of action based on the data may be determined. The results of the determination may be sent to one or more devices to provide feedback based on the physical characteristics of the subjects or to enable the device(s) to make an evaluation or determine a course of action based on the physical characteristics.

Additional objects, advantages, and novel features of the invention shall be set forth in part in the description that follows, and in part will become apparent to those skilled in the art upon examination of the following or may be learned by the practice of the invention.

According to embodiments of the present invention, a method for providing feedback includes receiving data indicative of a physical characteristic of a first subject and a physical characteristic of a second subject; determining an evaluation of the data; and providing a notification regarding the evaluation to a device. In other embodiments of the present invention, a method for providing feedback includes receiving data indicative of a physical characteristic of a plurality of subjects; determining a course of action based, at least in part, on the data; and providing a notification based, at least in part, on the course of action. In still further embodiments, a method for providing feedback includes determining a desired action associated with a group of subjects; receiving data indicative of a physical characteristic of at least one of the subjects; determining a course of action based, at least in part, on the characteristic and the desired action; and providing a notification based on the course of action.

According to another embodiment of the present invention, a system for facilitating feedback includes a memory; a communication port; and a processor connected to the memory and the communication port, the processor being operative to receive data indicative of a physical characteristic of a first subject and a physical characteristic of a second subject; determine an evaluation of the data; and provide a notification regarding the evaluation to device. In other embodiments of the present invention, a system for facilitating feedback includes a memory; a communication port; and a processor connected to the memory and the communication port, the processor being operative to receive data indicative of a physical characteristic of a plurality of subjects; determine a course of action based, at least in part, on the data; and provide a notification based, at least in part, on the course of action. In other embodiments of the present invention, a system for facilitating feedback includes a memory; a communication port; and a processor connected to the memory and the communication port, the processor being operative to determine a desired action associated with a group of subjects; receive data indicative of a physical characteristic of at least one of the subjects; determine a course of action based, at least in part, on the characteristic and the desired action; and provide a notification based on the course of action.

According to yet another further embodiment of the present invention, an apparatus for using feedback includes means for obtaining data representative of a physical characteristic of a first subject and a physical characteristic of a second subject; means for evaluating the data; and means for sending data indicative of the evaluation to a device. In other embodiments of the present invention, an apparatus for using feedback includes means for obtaining data indicative of a physical characteristic of a plurality of subjects; means for identifying a course of action based, at least in part, on the data; and means for sending a notification based, at least in part, on the course of action. In other embodiments of the present invention, an apparatus for using feedback includes means for identifying a desired action associated with a group of subjects; means for obtaining data indicative of a physical characteristic of at least one of the subjects; means for identifying a course of action based, at least in part, on the characteristic and the desired action; and means for sending a notification based on the course of action.

According to a further embodiment of the present invention, a computer program product in a computer readable medium for using feedback includes first instructions for obtaining receiving data representative of a physical characteristic of a first subject and a physical characteristic of a second subject; second instructions for evaluating the data; and third instructions for sending data indicative of the evaluation to a device. In other embodiments of the present invention, a computer program product in a computer readable medium for using feedback includes first instructions for obtaining data indicative of a physical characteristic of a plurality of subjects; second instructions for identifying a course of action based, at least in part, on the data; and third instructions for sending a notification based, at least in part, on the course of action. In other embodiments of the present invention, a computer program product in a computer readable medium for using feedback first instructions for identifying a desired action associated with a group of subjects; second instructions for obtaining data indicative of a physical characteristic of at least one of the subjects; third instructions for identifying a course of action based, at least in part, on the characteristic and the desired action; and fourth instructions for sending a notification based on the course of action.

With these and other advantages and features of the invention that will become hereinafter apparent, the nature of the invention may be more clearly understood by reference to the following detailed description of the invention, the appended claims and to the several drawings attached herein.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

FIG. 8 is an illustration of one possible implementation of the evaluation database of FIG. 5.

DETAILED DESCRIPTION

Applicants have recognized that there is a need for systems and methods that allow for biometric information and other physical characteristic data to be obtained regarding two or more subjects and evaluate or determine a course of action or evaluation based on the information and data. For example, assume a speaker is giving a presentation to an audience of ten people and that the speaker may want to direct the presentation along one of several potential themes depending on the interest of the audience. In the method of the present invention, information regarding each of the audience member's heart rates, posture, etc. may be obtained and used to help determine which of the themes the audience members are the most interested in. Once the information is communicated to the speaker, the speaker can direct the presentation appropriately.

Applicants have also recognized that there is a need for systems and methods that enable a desired action associated with a group of subjects to be determined to be obtained by obtaining biometric information and other physical characteristic data to be obtained from or about the group and using such information and data to help determine a course of action that will lead to or produce the desired action. For example, a math instructor may desire that students in a classroom memorize multiplication tables. Sensors may obtain information from two or more of the students regarding brain wave patterns, amount of movement (e.g., an indication of restlessness), heart and respiration rates, etc. Based on this information, a determination may be made as to a course of action the instructor should take to increase the chances of getting students to memorize the multiplication tables. For example, students who are determined to be bored or sleepy (e.g., have relatively slow heart rates, have not shifted position recently) may need to engage in a physical activity to wake them up or make them more alert prior to studying the multiplication tables. Students who are very active (e.g., have relatively high heart rates, are very fidgety) may need to be calmed down before beginning to memorize multiplication tables. Once the determination of a course of action is made, it can be provided to the instructor so that the instructor can proceed accordingly with an improved chance of reaching the desired activity.

These and other features will be discussed in further detail below, by describing a system, individual devices, and processes according to embodiments of the invention.

Process Description

Figure 1:
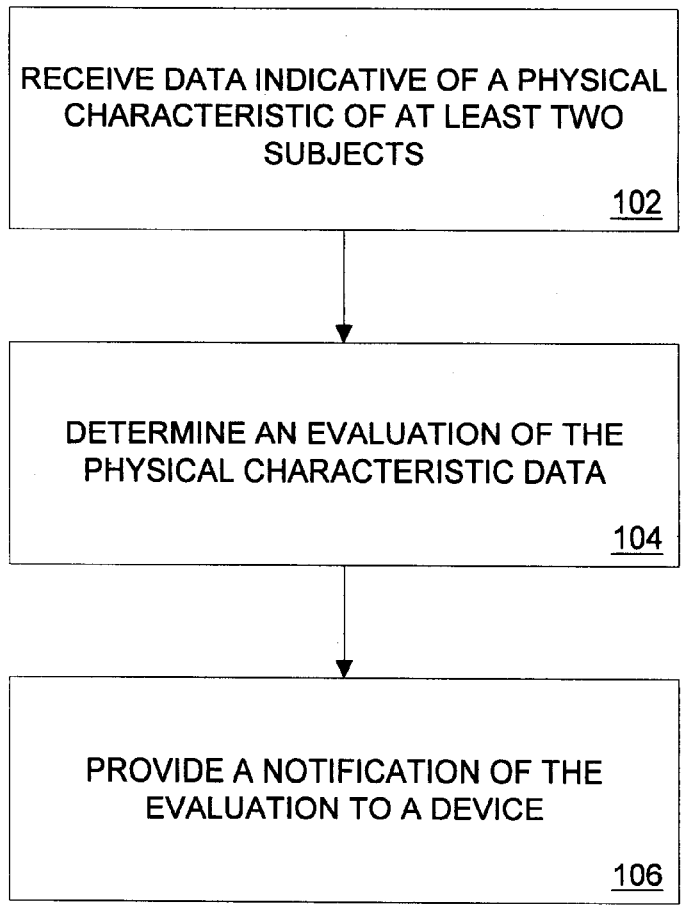
FIG. 1 is a flowchart of a first embodiment of a method in accordance with the present invention.

Reference is now made to FIG. 1, where a flow chart 100 is shown which represents the operation of an embodiment of the present invention. The particular arrangement of elements in the flow chart 100 is not meant to imply a fixed order to the steps; embodiments of the present invention can be practiced in any order that is practicable. In some embodiments, some or all of the steps of the method 100 can be implemented by a server or other device.

Processing begins at a step 102 during which data indicative of one or more physical characteristics of two or more subjects (e.g., human beings, animals) is obtained or otherwise received. A physical characteristic of a subject might be or include the subjects' heart rate, blood pressure, blood sugar level, posture, temperature, respiration rate, facial response or position, weight, height, galvanic skin response, pheromone emission, brain wave pattern, odor, motion, etc., or a change in any one or more of them.

The physical characteristic of one subject for which data is received during the step 102 may be the same as or different from the physical characteristic for which data is received for another subject during the step 102. For example, during the step 102, data might be received regarding the heart rate of one subject and the respiration and/or heart rate of a second subject. Data from more than one subject might be received simultaneously from multiple subjects during the step 102 or from different subjects at different periods of time during the step 102. The data for different subjects can come from different sources or sensors, be in different formats and contain information regarding the same or different physical characteristics. In some embodiments, information regarding one or more sensors may be stored in, and accessed from, a sensor information database.

Data and other information regarding physical characteristics of a subject can be obtained directly or indirectly by having the subject wear, carry or hold a sensor or other data gathering device (e.g., heart rate sensor, blood pressure monitor, motion sensor), by having the subject sit in a chair having sensors or data gathering devices mounted in it or attached to it, etc. Thus, a sensor might be associated with a specific subject and provide data regarding only that subject. In some embodiments, a sensor or other data gathering device might detect or obtain data indicative of a physical characteristic for more than one subject. Data regarding or indicative of one or more physical characteristics of one or more subjects also may be received during the step 102 from observers watching the subject(s) and making, entering or recording observations.

During a step 104, an evaluation is determined of the physical characteristic(s) for which data was received during the step 102 regarding one or more of the subjects for which data was received during the step 102. The determination or evaluation may occur in a variety of ways and the evaluation may be directed toward a variety of behaviors. For example, based on the information received during the step 102 for a subject, the determination performed during the step 104 may include determining a risk of violence associated with one or more of the subjects, determining one or more options to provide to one or more of the subjects, determining a trading propensity associated with one or more of the subjects, predicting at least one action or course of action that might be taken or contemplated by one or more of the subjects (e.g., is the subject likely to leave the room) or is desired to be taken by one or more of the subjects, determining a probability associated with an action or course of action that might be taken, or is desired to be taken, by one or more of the subjects (e.g., how likely is a subject to leave the room, how likely is a subject to stop paying attention to a speaker, how likely is a subject to fall asleep), etc. In some embodiments, information regarding one or more evaluations may be stored in, or accessed from, an evaluation database.

In some embodiments, the step 104 may include determining one or more options to provide to a subject or a group of subjects. For example, the method 100 may include a step of receiving a notification of several possible endings to a play being presented to an audience. The step 104 may include determining which of the options to provide to the audience or determining which of the options the audience will be allowed to choose from. Suppose five possible endings are available for the play, two of which are happy endings and three or which are sad endings. If the audience appears or is determined to want a happy ending, the audience may be provided with the two options having happy endings for the play. If instead the audiences appears or is determined to want a sad ending, the audience may be provided with the three options having a sad ending for the play. A notification of the possible options may be provided to one or more of the audience members to allow them to make the selection on the desired ending.

In some embodiments, the determination made during the step 104 may include determining what type of response to provide to a subject or group of subjects. For example, two or more subjects may be part of a group listening to a live lecture or training seminar. The data received during the step 102 may indicate that one or more of the subjects is sleepy, bored, restless, confused, etc. Thus, an evaluation of the data may indicate that the person conducting the lecture or seminar should change the responses given to questions asked by the subject(s) in order to hold the subjects' interest better and provide more effective instruction to the subject(s). In addition, the evaluation may indicate that the conductor should provide different information to the subjects (e.g., raise or lower the sophistication of the presentation to better match the subjects' interests, background, education, topic familiarity, etc.). As another example, the evaluation determined during the step 104 may indicate that a break or interruption is needed so that the subjects can stretch their legs, use the restroom, overcome boredom or fatigue, etc.

The determination made during the step 104 might include comparing the data received during the step 102 with stored records or examples of previously gathered data and associated behaviors or evaluations. The records or examples may be stored in a database. For example, the data collected during the step 102 may be from two or more subjects watching a new television show. The producers of the show may be trying to evaluate which ending to use for the show based on the subjects' reaction to earlier parts of the show. Thus, the step 104 may include determining a course of entertainment or response to provide to a subject. The data received during the step 102 may include heart rate information, respiration rate information, etc. By comparing the data received during the step 102 to data received for the subjects when they watched previous shows, the producers may be able to determine the subject's level of interest during various parts of the current show. Alternatively, by comparing the data received during the step 102 to data from other subjects who watched the same show, the producers may be able to predict what parts of the current show most interest the current subjects.

In some embodiments, determining an evaluation during the step 104 may include determining an environmental condition to alter or select. For example, the data received during the step 102 may indicate that some or all of a group of subjects are cold based on temperature and facial response information collected from the subjects. Thus, the determination made during the step 104 may be to increase the room temperature so as to improve the mood and enjoyment of the subjects.

In some embodiments, the evaluation determined during the step 104 may be or include an aggregating or averaging of data taken or received from multiple subjects or some other manipulation or transformation of the data. For example, the evaluation determined during the step 104 may be or include finding the average heart rate for a group of subjects, the average maximum and/or minimum heart rate for a group of subjects, the average respiration rate for the group of subjects, etc. Thus, determining an evaluation during the step 104 may be or include summarizing, tabulating, charting, collecting, aggregating, averaging, comparing, correlating, etc. some or all of the raw physical characteristic data received during the step 102. The evaluation may use other information in addition to the data received during the step 102. As another example, determining an evaluation during the step 104 may be or include determining the total number of people in a room who have moved, yawned, slept, undergone a decrease/increase in heart rate or respiration rate, etc. during a given time period. Thus, determining an evaluation during the step 104 may be or include collecting and preparing for later use the raw data received during the step 102 and/or a processed or altered version of the raw data received during the step 102.

In some embodiments, determining an evaluation during the step 104 may be or include determining a pattern in data received during the step 102 from two or more subjects regarding one or more physical characteristics.

During a step 106, a notification of the evaluation determined during the step 104 is provided to at least one device. The notification provided during the step 106 can be sent to more than one device and more than one type of device. The notification may be or include an email message, instant message communication, electronic signal or other communication (e.g., radio or wireless transmission, FTP, HTTP or HTML transmission, XML feed), an audible sound, a visual display, a voice message, etc. The notification may be sent to a variety of devices such as, for example, ear phones, a speaker, a software program operating on a device, an electronic storage device (e.g., hard disk drive, CD-ROM drive), a server, and a user device (e.g., personal digital assistant, computer). The notification may be or include a summary, table, chart, correlation, comparison, graph, etc of some or all of the data received during the step 102. In some embodiments, information regarding the notification or devices the notification is sent to may be stored in, or accessed from, an output or notification database.

As one example of the step 106, assume a speaker is giving a lecture to a group of subjects. Data received from the subjects during the step 102 and evaluated during the step 104 may provide guidance as to what parts of the lecture the group is most interested in. Once the evaluation is determined during the step 104, a notification of the evaluation may be sent to a computer being used by the speaker and displayed on the computer's screen as raw data, as a histogram, chart, graph, etc. Alternatively, the speaker may be wearing an ear phone that can pick up a wireless signal containing the notification. The audible notification may be created by a text-to-speech converter that converts the evaluation determined during the step 104 to a signal that is sent to the speaker's ear phone.

In some embodiments of the method 100, the notification sent during the step 106 may include a suggested course of action based on the evaluation determined during the step 104 or the characteristic data received during the step 102. Thus, the method 100 may include a step during which a suggested course of action is determined. For example, the data received during the step 102 may be indicative of heart rates, blood pressures, fidgetiness or restlessness, etc. for a group of subjects listening to a training lecture. The determination made during the step 104 of the data received during the step 102 may indicate that the group of subjects may be bored or in need of a break. Based on this evaluation and or characteristic data of the subjects, a determination may be made that a ten-minute break should be given. The notification sent during the step 106 may include the suggestion or another notification may be sent after the step 106 that includes the suggestion.

In some embodiments, the method 100 may include a step of determining a desired action to be taken by a subject or group of subjects. Such a step may be completed before or after the step 102. Thus, the evaluation determined during the step 104 may be directed to getting the subject or group of subjects to initiate, perform or complete the desired action based on the physical characteristic data received during the step 102.

Figure 2:
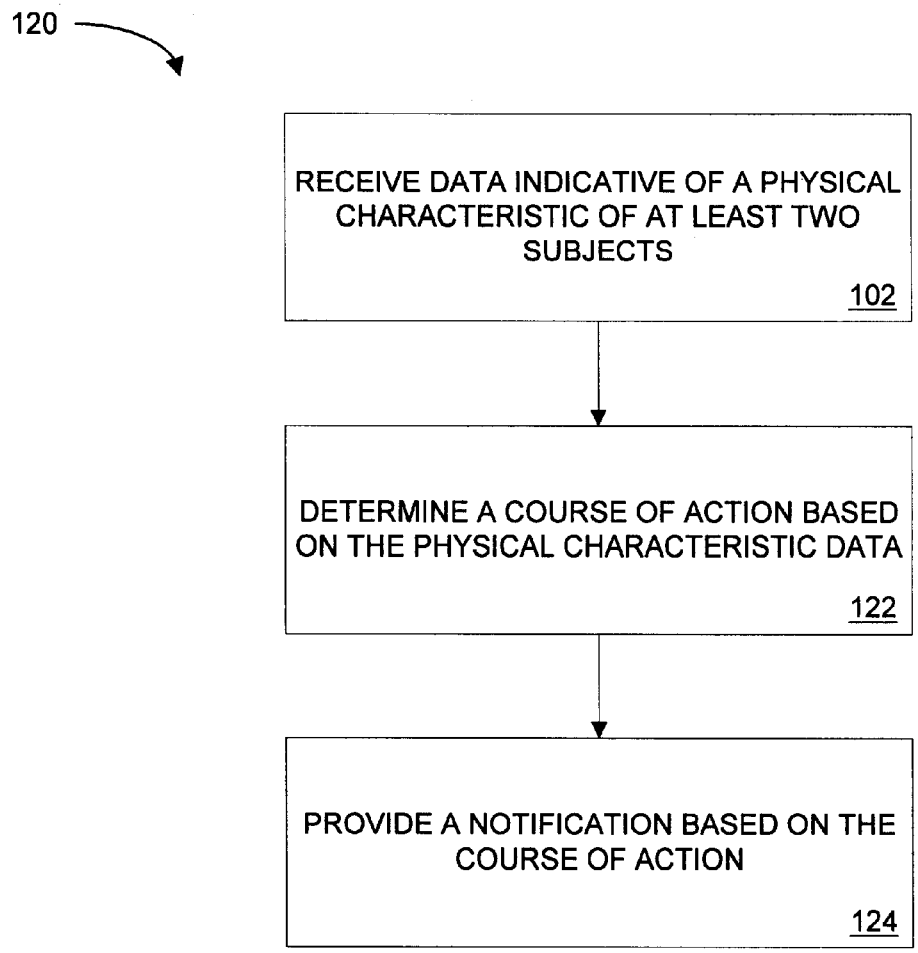
FIG. 2 is a flowchart of a second embodiment of a method in accordance with the present invention.

Reference is now made to FIG. 2, where a flow chart 120 is shown which represents the operation of an embodiment of the present invention. The particular arrangement of elements in the flow chart 120 is not meant to imply a fixed order to the steps; embodiments of the present invention can be practiced in any order that is practicable. In some embodiments, some or all of the steps of the method 120 can be implemented by a server or other device.

The method 120 includes the step 102 as previously discussed above. In addition, after the step 102 the method includes a step 122 during which a course of action is determined based on the characteristic data received during the step 102. For example, a storyteller may be telling a series of stories. The data received during the step 102 may be indicative of heart rate, respiration rate, etc. for one or more people in the audience. The data can be used to determine which type of story the audience likes the best, the preferred length of stories, etc. Thus, a course of action may be determined that suggests what type of stories the audience is most interested in and how the long the stories should be for the storyteller. A database may exist of different stories that the storyteller can provide and, as a result, the course of action determined during the step 122 may include a list of stories, and perhaps a desired sequence of stories, that the storyteller can recite to the audience.

As another example, a film may be presented to an audience of people. The film may have a variety of possible endings. Data regarding physical characteristics of the audience members received during the step 102 may be used during the step 122 to determine which specific ending to provide to this particular audience.

The determination made during the step 122 may be performed by comparing the data received during the step 102 to stored records of behaviors and associated physical characteristics.

During a step 124, a notification is provided regarding the course of action determined during the step 122. The step 124 is similar to the step 106 previously discussed above. The notification may be sent to a variety of devices in a variety of formats. The notification provided during the step 124 may be sent in any format or form, including, but not limited to, HTTP, HTML or FTP transmission, XML feed, email message, instant message communication, facsimile transmission, telephone call, electronic signal or communication, etc., and may be sent to any type of device, such as a server or user device (e.g., computer, cellular telephone). In some embodiments, the notification may be sent to different devices depending on the course of action determined during the step 122.

In some embodiments, the method 120 may include a step of determining a desired action to be taken by one or more of a group of subjects, as previously discussed above with regard to the method 100. Thus, the course of action determined during the step 122 may be directed to getting a subject or group of subjects to perform or complete the desired action based on the physical characteristic data received during the step 102 for two or more of the subjects.

Figure 3:
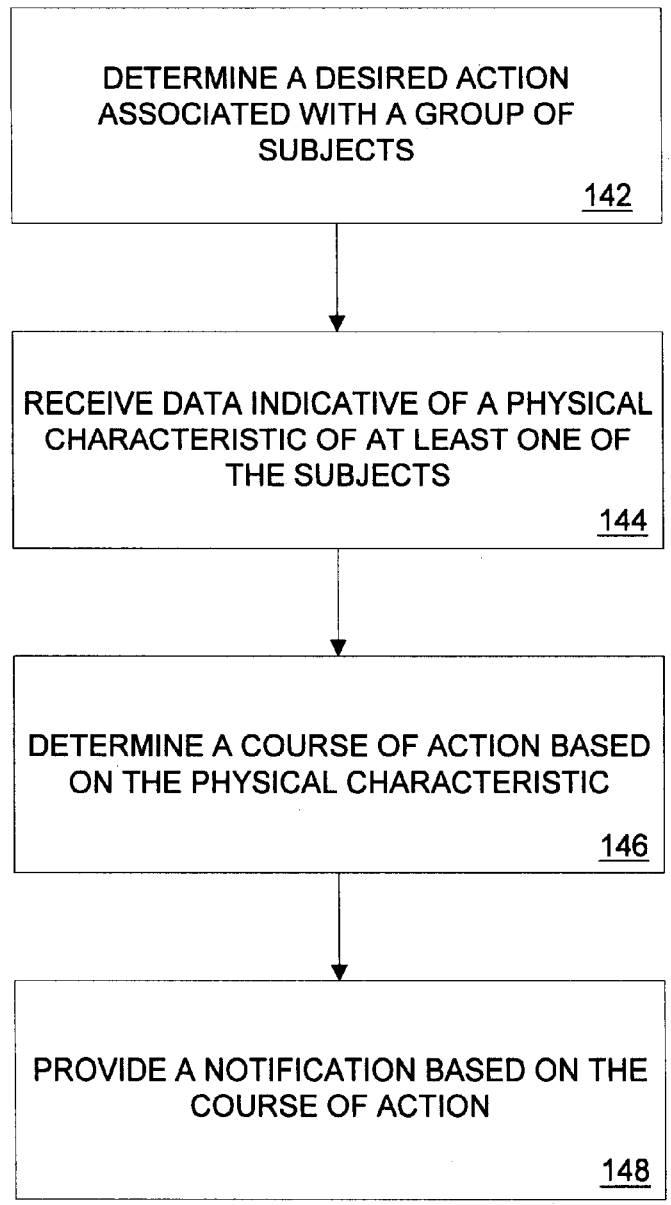
FIG. 3 is a flowchart of a third embodiment of a method in accordance with the present invention.

Reference is now made to FIG. 3, where a flow chart 140 is shown which represents the operation of an embodiment of the present invention. The particular arrangement of elements in the flow chart 140 is not meant to imply a fixed order to the steps; embodiments of the present invention can be practiced in any order that is practicable. In some embodiments, some or all of the steps of the method 140 can be implemented by a server or other device.

The method 140 includes a step 142 during which a desired action associated with a group of subjects is determined. For example, a motivational speaker may want to get a group of audience members to stand up and applaud and a specific time during a presentation. As another example, a researcher conducting a psychological examination via computer of a group of people may want to have the people communicate with each other at a specific time.

During a step 144, data indicative of one or more physical characteristics of at least one of the subjects is received. The step 144 is similar to the step 102 previously discussed above.

During a step 146, a course of action is determined based on the physical characteristic(s) for which data was received during the step 144. In addition, the course of action may be based on the desired action determined during the step 142. The course of action determined during the step 146 may be selected so as to improve the chances of a subject or group of subjects completing the action determined during the step 142 based on the physical characteristic data received during the step 144 for one or more of the subjects.

During a step 148, a notification regarding the course of action is provided. The step 148 is similar to the step 124 previously discussed above. The notification may be provided in any form or format.

System

Figure 4:
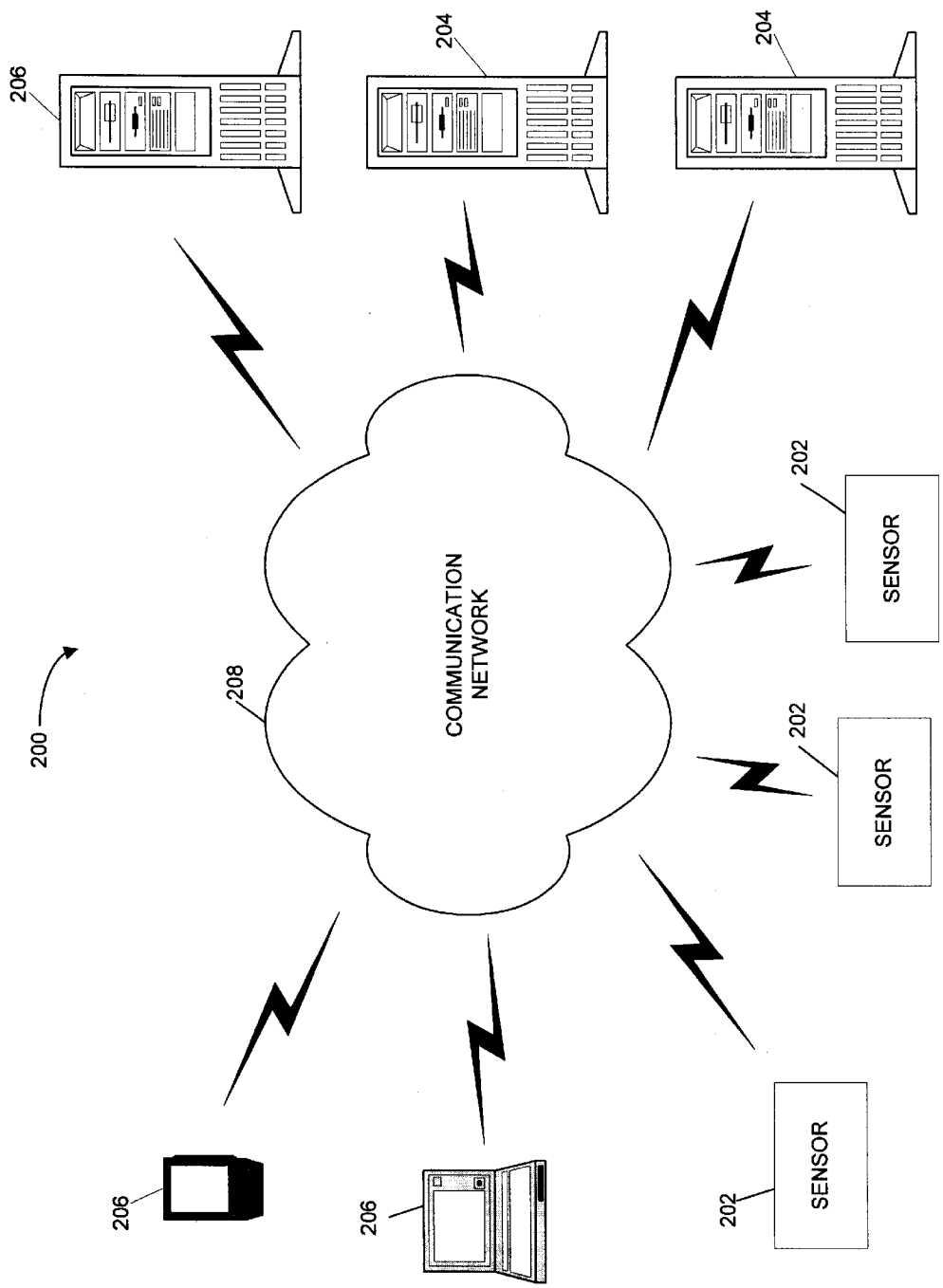
FIG. 4 is a block diagram of system components for an embodiment of an apparatus usable with the methods of FIGS. 1–3.

Now referring to FIG. 4, an apparatus or system 200 usable with the methods 100, 120 and 140 is illustrated. The apparatus 200 includes one or more sensors 202 that may communicate directly or indirectly with one or more servers, controllers or other devices 204, and one or more user devices 206 that may communicate with a server 204, via a computer, data, or communications network 208. For purposes of further explanation and elaboration of the methods 100, 120 and 140, the method 100, 120 and 140 will be assumed to be operating on, or under the control of, one the servers 204.

In some embodiments, a server 204 may implement or host a Web site. A server 204 can comprise a single device or computer, a networked set or group of devices or computers, a workstation, etc. In some embodiments, a server 204 also may function as a database server, sensor controller, and/or as a user device. The use, configuration and operation of servers will be discussed in more detail below.

The sensors 202 preferably allow data to be obtained from one or more subjects regarding one or more physical characteristics of the subject(s). The sensors 202 may send data regarding physical characteristics to one or more of the servers 204 and or one or more of the user devices 206. In some embodiments, a sensor 202 may be worn, carried or handled by a subject or otherwise in contact with the subject. In other embodiments, a sensor 202 may form part of chair or other piece of furniture a subject is sitting in, resting or standing on, etc. In some embodiments, a sensor 202 may be not be in contact with a subject. For example, a heat sensor (e.g., an infrared signal detector) may be used to detect an amount of heat or energy being created by a subject, even though the sensor is not in contact with the subject.

There are many kinds of sensors that might be used with the apparatus 200. Potential sensors include heart rate monitors, blood pressure monitors, respiration rate monitors, water or perspiration detectors, temperature or heat detectors, pressure sensors, load sensors, motion detectors, acceleration sensors, brain wave monitors, etc.

The user devices 206 allow users to interact with the server 204 and the remainder of the apparatus 200. The user devices 206 also may enable a user or entity to access Web sites, software, databases, sensor data, etc. hosted or operated by, or stored on, the servers 204 and to receive communications or other notifications sent by the servers 204. If desired, the user devices 206 also may be connected to or otherwise in communication with other devices. Possible user devices include a personal computer, portable computer, mobile or fixed user station, workstation, network terminal or server, cellular telephone, kiosk, dumb terminal, personal digital assistant, radio, two-way pager, etc. In some embodiments, a user device 206 also may function as a server 204.

Many different types of implementations or hardware configurations can be used in the system 200 and with the methods 100, 120, 140 and the methods disclosed herein are not limited to any specific hardware configuration for the system 200 or any of its components.

The communications network 208 might be or include the Internet, the World Wide Web, or some other public or private computer, cable, telephone or communications network or intranet, as will be described in further detail below. The communications network 208 illustrated in FIG. 4 is only meant to be generally representative of cable, computer, telephone or other communication networks for purposes of elaboration and explanation of the present invention and other devices, networks, etc. may be connected to the communications network 208 without departing from the scope of the present invention. The communications network 208 can also include other public and/or private wide area networks, local area networks, wireless networks, data communication networks or connections, intranets, routers, satellite links, microwave links, cellular or telephone networks, radio links, fiber optic transmission lines, ISDN lines, T1 lines, DSL, etc. In some embodiments, a user device 206 or sensor 202 may be connected directly to a server 204 or a user device 206 without departing from the scope of the present invention. Moreover, as used herein, communications include those enabled by wired or wireless technology.

In some embodiments, a suitable wireless communication network 208 may include the use of Bluetooth technology, allowing a wide range of computing and telecommunication devices to be interconnected via wireless connections. Specifications and other information regarding Bluetooth technology are available at the Bluetooth Internet site www-.bluetooth.com. In embodiments utilizing Bluetooth technology, some or all of the devices of FIG. 4 may be equipped with a microchip transceiver that transmits and receives in a previously unused frequency band of 2.45 GHz that is available globally (with some variation of bandwidth in different countries). In addition to data, up to three voice channels are available. Connections can be point-to-point or multipoint over a current maximum range of ten (10) meters. Embodiments using Bluetooth technology may require the additional use of one or more receiving stations to receive and forward data from individual sensors 202, user devices 206 or servers 204.

Although three sensors 202, three user devices 206, and two servers 204 are shown in FIG. 4, any number of such devices may be included in the system 200. The devices shown in FIG. 4 need not be in constant communication. For example, a user device or sensor may communicate with a server only when such communication is appropriate or necessary.

Server

Figure 5:
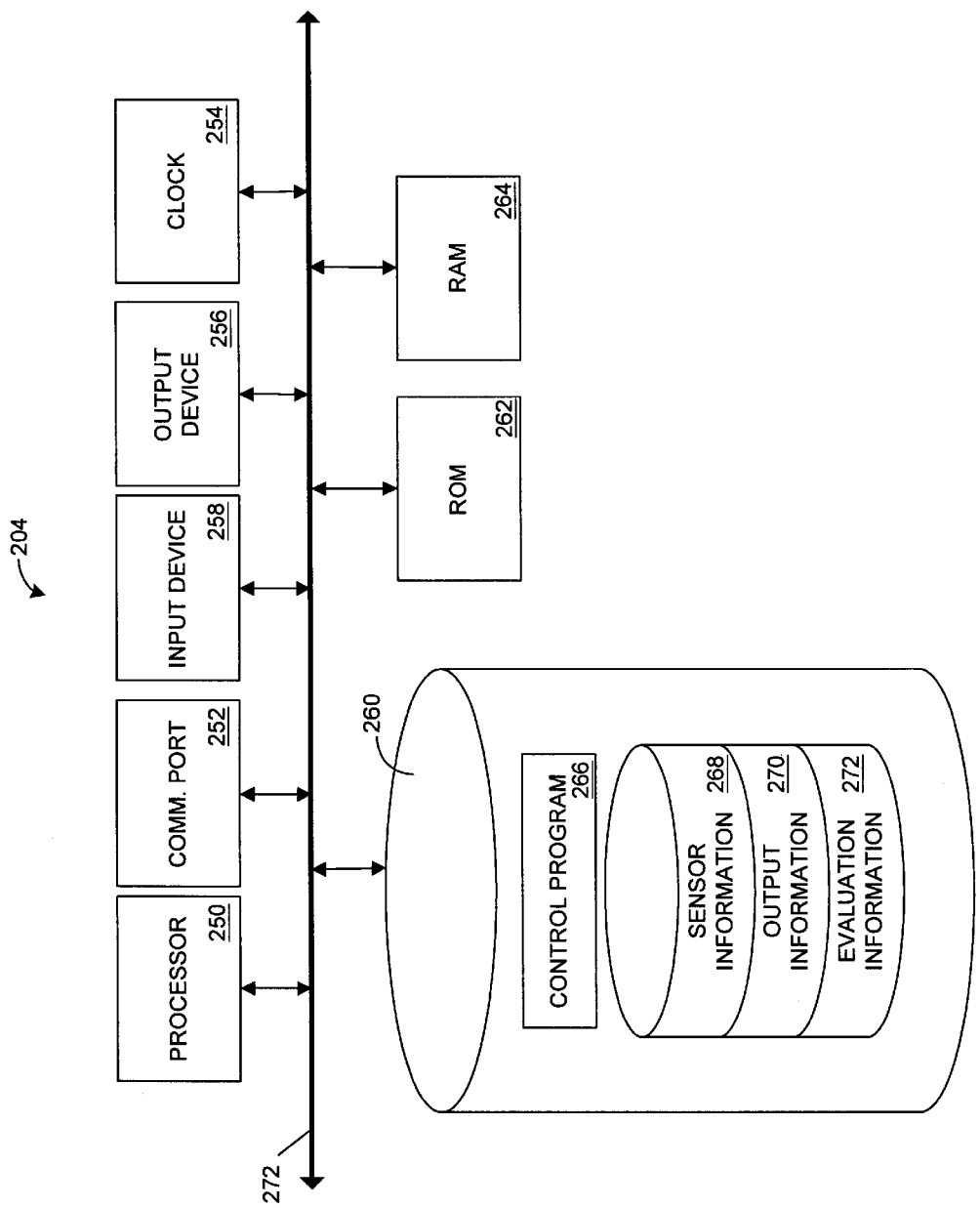
FIG. 5 is a block diagram of a representative server of FIG. 4.

Now referring to FIG. 5, a representative block diagram of a server or controller 204 is illustrated. The server 204 may include a processor, microchip, central processing unit, or computer 250 that is in communication with or otherwise uses or includes one or more communication ports 252 for communicating with user devices and/or other devices.

Communication ports may include such things as local area network adapters, wireless communication devices, Bluetooth technology, etc. The server 204 also may include an internal clock element 254 to maintain an accurate time and date for the server 204, create time stamps for data, notifications and other communications received or sent by the server 204, etc.

If desired, the server 204 may include one or more output devices 256 such as a printer, infrared or other transmitter, antenna, audio speaker, display screen or monitor, text to speech converter, etc., as well as one or more input devices 258 such as a bar code reader or other optical scanner, infrared or other receiver, antenna, magnetic stripe reader, image scanner, roller ball, touch pad, joystick, touch screen, microphone, computer keyboard, computer mouse, etc.

In addition to the above, the server 204 may include a memory or data storage device 260 to store information, software, databases, notifications and communications, device drivers, sensor data, potential responses or courses of action, etc. The memory or data storage device 260 preferably comprises an appropriate combination of magnetic, optical and/or semiconductor memory, and may include, for example, Random Read-Only Memory (ROM), Random Access Memory (RAM), a tape drive, flash memory, a floppy disk drive, a Zip™ disk drive, a compact disc drive, DVD drive, and/or a hard disk drive. The server 204 might also include ROM 262 and RAM 264 for additional storage and memory.

The processor 250 and the data storage device 260 in the server 204 each may be, for example: (i) located entirely within a single computer or other computing device; or (ii) connected to each other by a remote communication medium, such as a serial port cable, telephone line or radio frequency transceiver. In one embodiment, the server 204 may comprise one or more computers that are connected to a remote server computer for maintaining databases.

A conventional personal computer or workstation with sufficient memory and processing capability may be used as the server 204. In one embodiment, the server 204 operates as or includes a Web server for an Internet environment. The server 204 preferably is capable of high volume transaction processing, performing a significant number of mathematical calculations in processing communications and database searches. A Pentium™ microprocessor such as the Pentium III™ microprocessor, manufactured by Intel Corporation may be used for the processor 250. Equivalent processors are available from Motorola, Inc., AMD, or Sun Microsystems, Inc. The processor 250 also may comprise one or more microprocessors, computers, computer systems, etc.

Software may be resident and operating or operational on the server 204. The software may be stored on the data storage device 260 and may include a control program 266 for operating the server, databases, etc. The control program 266 may control the processor 250. The processor 250 preferably performs instructions of the control program 266, and thereby operates in accordance with the present invention, and particularly in accordance with the methods described in detail herein. The control program 266 may be stored in a compressed, uncompiled and/or encrypted format. The control program 266 furthermore includes program elements that may be necessary, such as an operating system, a database management system and device drivers for allowing the processor 250 to interface with peripheral devices, databases, etc. Appropriate program elements are known to those skilled in the art, and need not be described in detail herein.

The server 204 also may include or store information regarding sensors, evaluations, outputs, etc. For example, information regarding sensors may be stored in a sensor database 268 for use by the server 204, a user device, or another device or entity. Similarly, information regarding evaluation outputs and output devices might be stored in an output database 270 for use by the server 204, a user device or another device or entity. Information regarding evaluations may be stored in an evaluation database 272 for use by the server or another device or entity. In some embodiments, a server 204, a user device, or other device also may store, use, or access a subject database to keep information about one or more subjects, the data being collected from the subjects, subject activities, subject behavior patterns, evaluations, etc.

According to an embodiment of the present invention, the instructions of the control program may be read into a main memory from another computer-readable medium, such as from the ROM 262 to RAM 264. Execution of sequences of the instructions in the control program causes the processor 250 to perform the process steps described herein. In alternative embodiments, hard-wired circuitry may be used in place of, or in combination with, software instructions for implementation of some or all of the methods of the present invention. Thus, embodiments of the present invention are not limited to any specific combination of hardware and software.

The processor 250, communication port 252, clock 254, output device 256, input device 258, data storage device 260, ROM 262, and RAM 264 may communicate or be connected directly or indirectly in a variety of ways. For example, the processor 250, communication port 252, clock 254, output device 256, input device 258, data storage device 260, ROM 262, and RAM 264 may be connected via a bus 272.

While specific implementations and hardware configurations for servers 204 devices have been illustrated, it should be noted that other implementations and hardware configurations are possible and that no specific implementation or hardware configuration is needed. Thus, not all of the components illustrated in FIG. 5 may be needed for a server implementing the method 100, method 120, or the method 140. Therefore, many different types of implementations or hardware configurations can be used in the system 200 and the methods disclosed herein are not limited to any specific hardware configuration.

User Device

As mentioned above, user device 206 may be any of a number of different types of devices, including, but not limited to a personal computer, portable computer, mobile or fixed user station, workstation, network terminal or server, telephone, beeper, kiosk, dumb terminal, personal digital assistant, facsimile machine, radio, two-way pager, cable set-top box, etc. In some embodiments, a user device might be or include speakers, earphones, a signal detector or receiver, etc. If desired, the user device 206 also may function as a server 204. In some embodiments, a user device 206 may have the same structure, components or configuration as the server 204 illustrated in FIG. 5.

Databases

As previously discussed above, in some embodiments a server, user device, or other device may include or access a sensor database for storing or keeping information about sensors. One representative sensor database 300 is illustrated in FIG. 6.

The sensor database 300 may include a sensor identifier field 302 that may includes codes or other identifying information for one or more sensors and a sensor description field 304 that may include information describing the sensors identified in the field 302, such as information regarding a sensor's name, description, model number, tolerances, specifications, manufacturer, etc. The sensor database 300 also may include a sensor output field 306 that may include information regarding the type, timing and format of the information or other data generated or otherwise provided by the sensors identified in the field 302. Other or different fields also may be used in the sensor database 300. For example, a sensor database might include a field that stores information regarding one or more subjects associated with the sensor.

Figure 6:
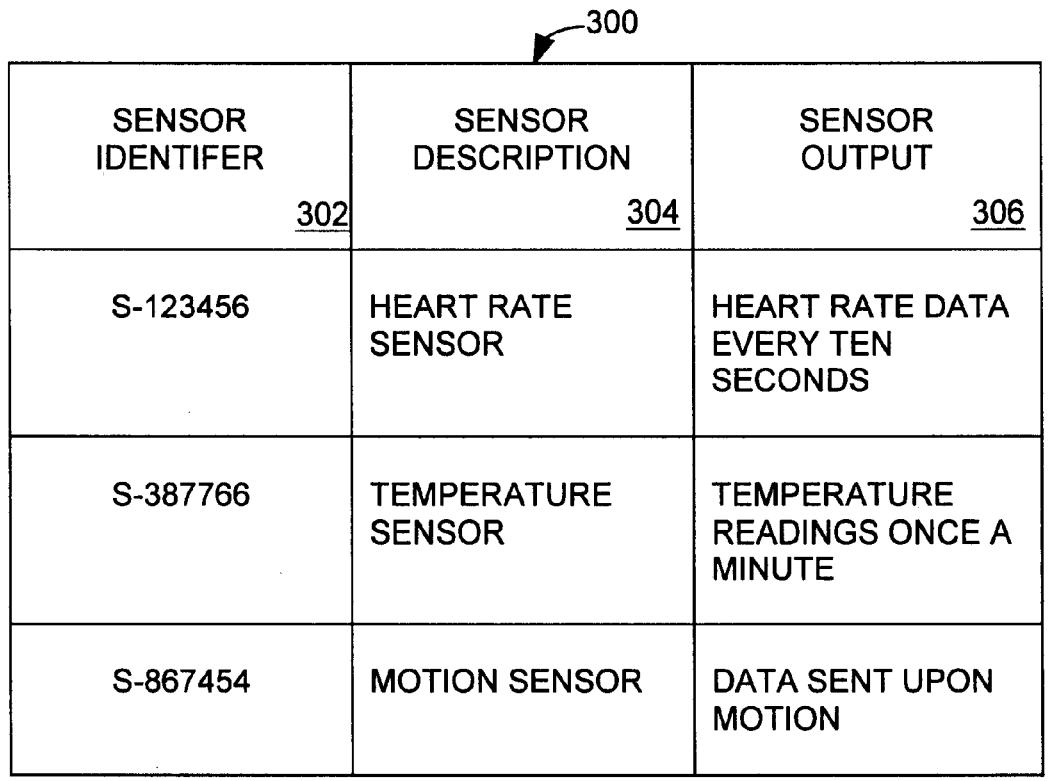
FIG. 6 is an illustration of one possible implementation of the sensor database of FIG. 5.

As illustrated in the sensor database 300 of FIG. 6, the sensor identified as "S-123456" in the field 302 is a heart rate sensor or monitor and provides heart rate data every ten seconds. The sensor identified as "S-867454" in the field 302 is a motion detector or sensor and provides data upon the detection of motion.

As previously discussed above, in some embodiments a server, user device, or other device may include or access an output database for storing or keeping information about information sent and received from one or more servers. One representative output database 400 is illustrated in FIG. 7.

The output database 400 may include an output identifier field 402 that contains codes or other identifying information regarding recipients of sensor data. The output database 400 also may include an output description field 404 that includes a name, identifier or other descriptive information for the output identifiers identified in the field 402 and a sensor identifier field 406 that identifies one or more sensors associated with the output identifiers provided in the field 402. Other or different fields also may be used in the output database 400. In some embodiments a specific output identifier might be associated with a specific evaluation to be determined or a specific course of action to be determined. Thus, the output database 400 might include a field that associates the devices identified in the field 402 with a specific determination being made or to be made.

Figure 7:
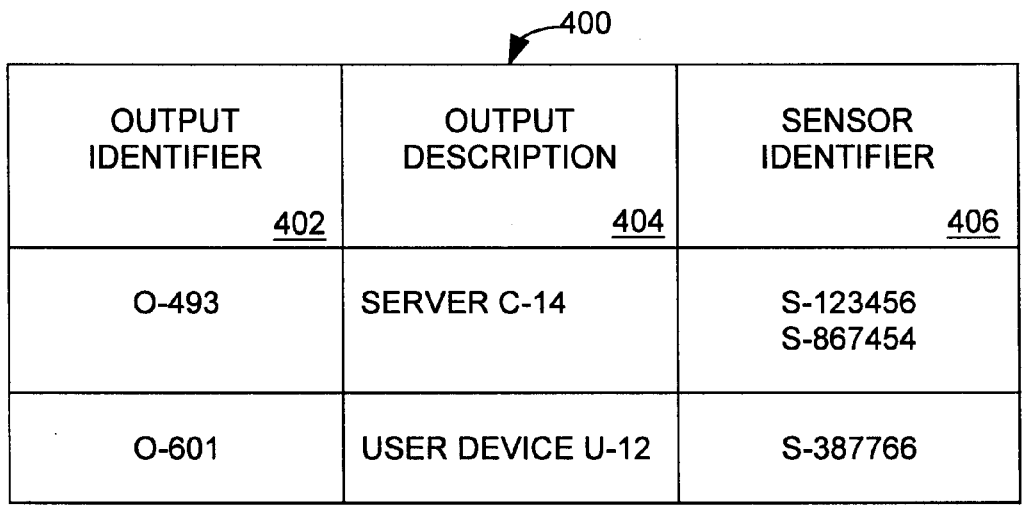
FIG. 7 is an illustration of one possible implementation of the output database of FIG. 5.

As illustrated in the output database 400 of FIG. 7, the output identified as "O-493" in the field 402 is "SERVER C-14" and is associated with the data provided by the sensors "S-123456" and "S-867454". Thus, the data provided by the sensors identified as "S-123456" and "S-867454", or a notification of an evaluation of the data provided by the sensors "S-123456" and "S-867454", is provided to or received by the "SERVER C14", which is identified as "O-493" in the field 402.

As previously discussed above, in some embodiments a server, user device, or other device may include or access an evaluation database for storing or keeping information about evaluations or courses of action to be determined. One representative evaluation database 500 is illustrated in FIG. 8.

The evaluation database 500 may include an evaluation identifier field 502 that may include codes or other identifying information for one or more evaluations or courses of action being determined. In addition, the evaluation database 500 also may include a description field 504 that may include information regarding the evaluations or courses of action identified in the field 502. In some embodiments the evaluation database 500 also may include a sensor identifier field 506 that may contain identifiers or other information regarding the sensor data to be used in the evaluations identified in the field 502. Other or different fields also may be used in the evaluation database 500.

As illustrated in the evaluation database 500 of FIG. 8, the evaluation identified as "E-0234" in the field 502 is an "INTEREST LEVEL DETERMINATION" based on data obtained or received from the sensors "S-123456" and "S-867454". Thus, during the determination during an implementation of the step 104, an evaluation is made using the data received during the step 102 from the sensors identified as "S-123456" and "S-867454" to determine if a subject or subject exhibits interest at one or more moments or during one or more periods of time.

In some embodiments a specific determination might be associated with a specific output device that will receive a notification of the determination. Thus, the evaluation database 500 might include a field that associates the evaluations identified in the field 502 with one or more devices that will receive information or other notifications regarding the evaluations.

The methods of the present invention may be embodied as a computer program developed using an object oriented language that allows the modeling of complex systems with modular objects to create abstractions that are representative of real world, physical objects and their interrelationships. However, it would be understood by one of ordinary skill in the art that the invention as described herein could be implemented in many different ways using a wide range of programming techniques as well as general-purpose hardware systems or dedicated controllers. In addition, many, if not all, of the steps for the methods described above are optional or can be combined or performed in one or more alternative orders or sequences without departing from the scope of the present invention and the claims should not be construed as being limited to any particular order or sequence, unless specifically indicated.

Each of the methods described above can be performed on a single computer, computer system, microprocessor, etc. In addition, two or more of the steps in each of the methods described above could be performed on two or more different computers, computer systems, microprocessors, etc., some or all of which may be locally or remotely configured. The methods 100, 120 and 140 can be implemented in any sort or implementation of computer software, program, sets of instructions, code, ASIC, or specially designed chips, logic gates, or other hardware structured to directly effect or implement such software, programs, sets of instructions or code. The computer software, program, sets of instructions or code can be storable, writeable, or savable on any computer usable or readable media or other program storage device or media such as a floppy or other magnetic or optical disk, magnetic or optical tape, CD-ROM, DVD, punch cards, paper tape, hard disk drive, Zip™ disk, flash or optical memory card, microprocessor, solid state memory device, RAM, EPROM, or ROM.

Although the present invention has been described with respect to a preferred embodiment thereof, those skilled in the art will note that various substitutions may be made to those embodiments described herein without departing from the spirit and scope of the present invention.

The words "comprise," "comprises," "comprising," "include," "including," and "includes" when used in this specification and in the following claims are intended to specify the presence of stated features, elements, integers, components, or steps, but they do not preclude the presence or addition of one or more other features, elements, integers, components, steps, or groups thereof.

The embodiments of the invention in which an exclusive property or privilege is claimed are defined as follows:

1. A method for providing feedback, comprising:
   receiving first data indicative of a physical characteristic of a first subject from a first device associated with said first subject and second data indicative of a physical characteristic of a second subject from a second device associated with said second subject;

determining an evaluation of said first data and said second data, wherein said evaluation is representative of a state of both said first subject and said second subject; and providing a notification regarding said evaluation to a device.

2. The method of claim 1, wherein said physical characteristic of said first subject includes at least one of the following:

said first subject's heart rate;
said first subject's blood pressure;
said first subject's blood sugar level;
said first subject's posture;
said first subject's weight;
said first subject's height;
said first subject's temperature;
said first subject's respiration rate;
a facial response of said first subject;
a galvanic skin response of said first subject;
a pheromone associated with said first subject;
a brain wave pattern of said first subject;
an odor generated by said first subject;
motion of said first subject;
a change in motion of said first subject;
a change in said first subject's heart rate;
a change in said first subject's blood pressure;
a change in said first subject's blood sugar level;
a change in said first subject's posture;
a change in said first subject's temperature;
a change in said first subject's respiration rate;
a change in a facial response of said first subject;
a change in a galvanic skin response of said first subject;
a change in a pheromone associated with said first subject;
a change in a brain wave pattern of said first subject; and
a change in an odor generated by said first subject.

3. The method of claim 1, wherein said receiving first data indicative of a physical characteristic of a first subject includes at least one of the following:

receiving data from at least one observer of said first subject regarding at least one physical characteristic of said first subject;

receiving data indicative of at least one physical characteristic from at least one sensor worn by said first subject; and receiving data indicative of at least one physical characteristic from at least one sensor associated with said first subject.

4. The method of claim 1, further comprising:

receiving data indicative of one or more physical characteristics for each of a plurality of subjects, wherein said plurality of subjects includes said first subject and said second subject.

5. The method of claim 4, further comprising:

determining a pattern in said data indicative of one or more physical characteristics for each of a plurality of subjects.

6. The method of claim 5, further comprising:

providing a notification regarding said pattern to said device.

7. The method of claim 1, wherein said determining an evaluation of said first data and said second data includes at least one of the following:

determining an aggregation of data indicative of a physical characteristic for each of a plurality of subjects, said plurality of subjects including said first subject and said second subject and at least one other subject;

determining an averaging of data indicative of a physical characteristic for each of a plurality of subjects, said plurality of subjects including said first subject and said second subject and at least one other subject;

computing a result based on a function of said first data and said second data;

comparing said physical characteristic of said first subject with a stored record of behavior;

comparing said physical characteristic of said second subject with a stored record of behavior;

determining a prediction regarding at least one action that might be taken by at least one of said first subject and said second subject;

determining a risk of violence associated with at least one of said first subject and said second subject;

determining a trading propensity associated with at least one of said first subject and said second subject;

determining an action that may be taken by at least one of said first subject and said second subject;

determining an action that is desired to be taken by at least one of said first subject and said second subject;

determining a course of entertainment to provide to at least one of said first subject and said second subject;

determining probability associated with an action that might be taken by said first subject;

determining at least one response to provide at least one of said first subject and said second subject;

determining at least one option to offer at least one of said first subject and said second subject;

selecting entertainment to provide at least one of said first subject and said second subject;

selecting information to provide at least one of said first subject and said second subject;

selecting at least one environmental condition for at least one of said first subject and said second subject; and altering at least one environmental condition for at least one of said first subject and said second subject.

8. The method of claim 1, further comprising:

determining which of a plurality of devices to provide said notification.

9. The method of claim 8, further comprising:

identifying said plurality of devices.

10. The method of claim 1, wherein said device includes at least one of the following:

ear phones;
a speaker;
a software program;
a visual display device;
an electronic storage device;
a server; and
a user device.

11. The method of claim 1, wherein said notification includes at least one of the following:

an evaluation of said first data and said second data;
an email message;

a visual display;

an electronic signal;

an audible sound; and a voice message.

12. The method of claim 1, wherein said evaluation includes at least one of the following:

an aggregation of data indicative of a physical characteristic for each of a plurality of subjects;

an averaging of data indicative of a physical characteristic for each of a plurality of subjects;

a selection of a behavior associated with said physical characteristic of said first subject;

a selection of a behavior associated with said physical characteristic of said second subject;

a comparison of said physical characteristic of said first subject with a stored record of behavior;

a prediction regarding at least one action that might be taken by at least one of said first subject and said second subject;

a determination of a risk of violence associated with at least one of said first subject and said second subject;

a determination of a trading propensity associated with at least one of said first subject and said second subject;

a determination of a course of action;

a determination of a course of entertainment;

a determination of a probability associated with a course of action that might be taken by at least one of said first subject and said second subject;

a determination of at least one response to provide at least one of said first subject and said second subject;

a determination of a least one response to subject said first subject to;

a determination of a least one response to subject said first subject to;

a determination of at least one option to offer at least one of said first subject and said second subject;

a selection of entertainment;

a selection of information; and a selection of at least one environmental condition.

13. The method of claim 1, further comprising:

receiving a notification regarding a plurality of options.

14. The method of claim 13, further comprising:

selecting one of said plurality of options based, at least in part, on said evaluation.

15. The method of claim 14, further comprising:

selecting said device based, at least in part, on said selecting one of said plurality of options.

16. The method of claim 13, wherein said device is associated with at least one of said plurality of options.

17. The method of claim 1, further comprising:

determining a course of action based on said first data and said second data.

18. The method of claim 17, further comprising:

providing a notification based on said course of action.

19. The method of claim 1, further comprising:

determining a course of action based on said evaluation.

20. The method of claim 19, further comprising:

providing a notification based on said course of action.

21. The method of claim 1, wherein said determining an evaluation of said first data and said second data includes comparing said physical characteristic of said first subject to at least one record of behavior associated with said physical characteristic of said first subject.

22. The method of claim 21, wherein said determining an evaluation includes determining a course of action based on said record of behavior.

23. The method of claim 1, further comprising:

determining a desired course of action and wherein said determining an evaluation of said first data and said second data includes determining an action based, at least in part on said data and said desired course of action.

24. The method of claim 1, wherein said physical characteristic of said first subject is the same as said physical characteristic of said second subject.

25. The method of claim 1, wherein said physical characteristic of said first subject is different from said physical characteristic of said second subject.

26. The method of claim 1, wherein said physical characteristic of said first subject is indicative of a response of said first subject to a first presentation.

27. The method of claim 26, wherein said physical characteristic of said second subject is indicative of a response of said second subject to a second presentation.

28. The method of claim 26, wherein said physical characteristic of said second subject is indicative of a response of said second subject to said first persentation.

29. The method of claim 1, wherein said first and second devices are the same.

30. The method of claim 1, wherein said first device is associated with more than one subject.

31. A method for providing feedback, comprising:

receiving data indicative of a physical characteristic of each of a plurality of subjects, wherein said physical characteristics of said subjects are indicative of responses of said subjects to a presentation;

determining a desired course of action associated with said plurality of subjects based, at least in part, on said data indicative of a physical characteristic of each of said plurality of subjects; and providing a notification based, at least in part, on said course of action.

32. The method of claim 31, wherein said determining a course of action based on said data indicative of a physical characteristic of each of a plurality of subjects includes one of the following:

determining a course of action based, at least in part, on said data indicative of a physical characteristic of each of a plurality of subjects and a desired action that can be taken by at least one of said plurality of subjects;

determining a course of action based, at least in part, on said data indicative of a physical characteristic of each of a plurality of subjects and a desired action that can be taken by said plurality of subjects; and determining at least one behavior associated with said physical characteristic.

33. The method of claim 31, further comprising:

determining a desired action to be taken by said plurality of subjects.

34. The method of claim 31, wherein said plurality of subjects includes a first subject and a second subject and wherein said data indicative of a physical characteristic of each of a plurality of subjects includes data indicative of a characteristic of said first subject and data indicative of a characteristic of said second subject.

35. The method of claim 31, wherein said characteristic of said first subject is different from said characteristic of said second subject.

36. A method for providing feedback, comprising:

determining a desired action associated with a group of subjects;

receiving data indicative of a physical characteristic of at least one of said group of subjects, wherein said physical characteristic of said at least one of said group of subjects is indicative of a response of said at least one of said group of subjects to a presentation;

determining a course of action expected to lead to said desired action based, at least in part, on said physical characteristic and said desired action; and providing a notification based on said course of action.

37. A system for facilitating feedback, comprising:

a memory;

a communication port; and a processor connected to said memory and said communication port, said processor being operative to:

receive first data indicative of a physical characteristic of a first subject and second data indicative of a physical characteristic of a second subject;

determine an evaluation of said first data and said second data, wherein said evaluation is representative of a state associated with both said first subject and said second subject; and provide a notification regarding said evaluation to device.

38. A computer program product in a computer readable medium for using feedback, comprising:

first instructions for obtaining receiving first data representative of a physical characteristic of a first subject and second data representative of a physical characteristic of a second subject;

second instructions for preparing an evaluation of said first data and said second data, wherein said evaluation is representative of a state associated with both said first subject and said second subject; and third instructions for sending third data indicative of said evaluation of said first data and said second data to a device.

39. A method for providing feedback, comprising:

receiving first data indicative of a physical characteristic of a first subject from a first device associated with said first subject and second data indicative of a physical characteristic of a second subject from a second device associated with said second subject;

determining an evaluation of said first data and said second data, wherein said determining said evaluation includes comparing said physical characteristic of said first subject to at least one record of behavior associated with said physical characteristic of said first subject; and providing a notification regarding said evaluation to a device.

40. The method of claim 39, wherein said determining an evaluation includes determining a course of action based on said at least one record of behavior.

41. The method of claim 39, wherein said determining said evaluation includes comparing said physical characteristic of said second subject to at least one record of behavior associated with said physical characteristic of said second subject.

* * * * *

US006701271C1

(12) EX PARTE REEXAMINATION CERTIFICATE (10753rd)
United States Patent
Willner et al.

(10) Number: US 6,701,271 C1
(45) Certificate Issued: Nov. 5, 2015

(54) METHOD AND APPARATUS FOR USING PHYSICAL CHARACTERISTIC DATA COLLECTED FROM TWO OR MORE SUBJECTS

(75) Inventors: Barry E. Willner, Briarcliff Manor, NY (US); Edith H. Stern, Yorktown Heights, NY (US); David P. Greene, Ossining, NY (US); Phillip Shi-lung Yu, Chappaqua, NY (US)

(73) Assignee: ICON HEALTH & FITNESS, INC., Logan, UT (US)

Reexamination Request:
No. 90/013,409, Feb. 6, 2015

Reexamination Certificate for:
Patent No.: 6,701,271
Issued: Mar. 2, 2004
Appl. No.: 09/859,827
Filed: May 17, 2001

(51) Int. Cl.
*A61B 5/00* (2006.01)
*G06F 19/00* (2011.01)
*G09B 23/00* (2006.01)
*G09B 23/28* (2006.01)

(52) U.S. Cl.
CPC ............ *A61B 5/0002* (2013.01); *G06F 19/322* (2013.01); *G06F 19/3418* (2013.01); *G06F 19/3487* (2013.01); *G09B 23/28* (2013.01)

(58) Field of Classification Search
None
See application file for complete search history.

(56) References Cited

To view the complete listing of prior art documents cited during the proceeding for Reexamination Control Number 90/013,409, please refer to the USPTO's public Patent Application Information Retrieval (PAIR) system under the Display References tab.

*Primary Examiner* — Matthew Heneghan

(57) ABSTRACT

A system, method, apparatus, and computer program code for using physical characteristic information obtained from two or more subjects to help evaluate subjects or to determine a course of action to take with the subjects includes receiving data indicative of one or more physical characteristics from two or more subjects, determining an evaluation of the data, and providing a notification to a device of the evaluation. A physical characteristic of a subject might be or include the subject's heart rate, blood pressure, blood sugar level, posture, temperature, respiration rate, facial response or position, weight, height, galvanic skin response, pheromone emission, brain wave pattern or rhythm, odor, motion, etc., or a change in any one or more of them.

At the time of issuance and publication of this certificate, the patent remains subject to pending reexamination control number 95/002,337 filed Sep. 14, 2012. The claim content of the patent may be subsequently revised if a reexamination certificate issues from the reexamination proceeding.

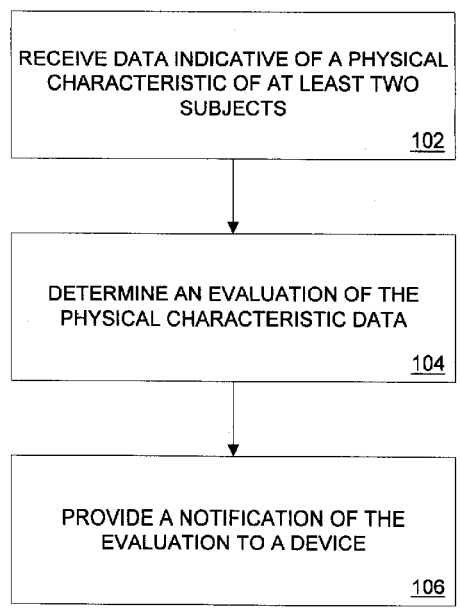

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE
SPECIFICATION AFFECTED BY AMENDMENT
ARE PRINTED HEREIN.

Column 10 line 36:

In some embodiments, a suitable wireless communication network 208 may include the use of [Bluetooth] *Bluetooth™ technology that operates in the 2.4 GHz industrial, scientific and medical (ISM) frequency band,* allowing a wide range of computing and telecommunication devices to be interconnected via wireless connections. Specifications and other information regarding [Bluetooth] *Bluetooth™* technology are available at the [Bluetooth] *Bluetooth™* Internet site www.bluetooth.com. In embodiments utilizing [Bluetooth] *Bluetooth™* technology, some or all of the devices of FIG. 4 may be equipped with a microchip transceiver that transmits and receives in a previously unused *ISM* frequency band of 2.45 GHz that is available globally (with some variation of bandwidth in different countries). In addition to data, up to three voice channels are available. Connections can be point-to-point or multipoint over a current maximum range of ten (10) meters. Embodiments using [Bluetooth] *Bluetooth™* technology may require the additional use of one or more receiving stations to receive and forward data from individual sensors 202, user devices 206 or servers 204.

Column 10, line 62:

Now referring to FIG. 5, a representative block diagram of a server or controller 204 is illustrated. The server 204 may include a processor, microchip, central processing unit, or computer 250 that is in communication with or otherwise uses or includes one or more communication ports 252 for communicating with user devices and/or other devices. Communication ports may include such things as local area network adapters, wireless communication devices, [Bluetooth] *Bluetooth™ technology that operates in the 2.4 GHz ISM frequency band,* etc. The server 204 also may include an internal clock element 254 to maintain an accurate time and date for the server 204, create time stamps for data, notifications and other communications received or sent by the server 204, etc.

AS A RESULT OF REEXAMINATION, IT HAS BEEN DETERMINED THAT:

Claim 1 is cancelled.

New claims 42-99 are added and determined to be patentable.

Claims 2-41 were not reexamined.

42. *The method of claim 1, wherein:*
*the first device is a first sensor;*
*the physical characteristic of the first subject is sensed by the first sensor;*
*the receiving of the first data includes a remote server receiving the first data from the first sensor through the Internet; and*
*the determining of the evaluation includes the remote server determining, based on the first data and based on the second data, which of multiple options to provide to the first subject for the first subject to select from.*

43. *The method of claim 42, wherein:*
*the determining, based on the first data and based on the second data, of which of multiple options to provide to the first subject for the first subject to select from includes determining, based on the first data and based on the second data, which of multiple endings to an event to provide to the first subject for the first subject to select from.*

44. *The method of claim 42, wherein:*
*the determining of the evaluation further includes the remote server determining, based on the first data and based on the second data, to provide different information to the first subject and to the second subject.*

45. *The method of claim 42, wherein:*
*the determining of the evaluation includes the remote server averaging the first data and the second data.*

46. *The method of claim 42, wherein:*
*the device is a device of a trainer of the first subject and the second subject.*

47. *The method of claim 46, wherein:*
*the evaluation is an audible notification; and*
*the device of the trainer is a wireless earphone.*

48. *The method of claim 42, wherein:*
*the device is a software application operating on a cellular telephone; and*
*the cellular telephone has a touch screen input device.*

49. *The method of claim 42, wherein:*
*the device is a software application operating on a portable computer; and*
*the portable computer has a touch screen input device.*

50. *The method of claim 42, wherein:*
*the device is a software application operating on a personal computer; and*
*the personal computer has a touch screen input device.*

51. *The method of claim 42, wherein:*
*the first sensor is a first portable wireless sensor;*
*the first sensor is configured to wirelessly connect with a cellular telephone through a wireless connection;*
*the cellular telephone is configured to wirelessly connect to the Internet through a wireless cellular connection; and*
*the remote server receiving of the first data from the first sensor through the Internet includes the remote server receiving the first data from the first sensor through the wireless connection between the first sensor and the cellular telephone and through the wireless cellular connection of the cellular telephone to the Internet.*

52. *The method of claim 51, wherein:*
*the wireless connection operates in the 2.4 GHz industrial, scientific and medical (ISM) frequency band.*

53. *The method of claim 51, wherein:*
*the wireless connection is an infrared wireless connection.*

54. *The method of claim 51, wherein:*
*the first portable wireless sensor is a heart rate sensor.*

55. *The method of claim 51, wherein:*
*the first portable wireless sensor includes a blood pressure sensor.*

56. *The method of claim 51, wherein:*
*the first portable wireless sensor includes a subject respiration rate sensor.*

57. The method of claim 51, wherein:
the first portable wireless sensor includes a subject weight sensor.
58. The method of claim 51, wherein:
the first portable wireless sensor includes a subject brain wave pattern sensor.
59. The method of claim 51, wherein:
the first portable wireless sensor includes a subject brain wave rhythm sensor.
60. The method of claim 51, wherein:
the first portable wireless sensor includes a subject motion sensor.
61. The method of claim 51, wherein:
the first portable wireless sensor includes a subject acceleration sensor.
62. The method of claim 42, wherein:
the first sensor is physically connected to a cellular telephone;
the cellular telephone is configured to wirelessly connect to the Internet over a wireless cellular connection; and
the remote server receiving of the first data from the first sensor through the Internet includes the remote server receiving the first data from the first sensor over the wireless cellular connection of the cellular telephone to the Internet.
63. The method of claim 62, wherein:
the first sensor is an acceleration sensor.
64. The method of claim 62, wherein:
the first sensor is a heart rate sensor.
65. The method of claim 62, wherein:
the first sensor is a temperature sensor.
66. The method of claim 42, wherein:
the first sensor is a first portable wireless sensor; and
the remote server receiving of the first data from the first sensor through the Internet includes the remote server receiving the first data from the first sensor over a first wireless connection to the Internet.
67. The method of claim 66, wherein:
the first wireless connection employs a first wireless receiving station that is connected to the Internet.
68. The method of claim 42, wherein:
the first sensor is formed in a stationary apparatus; and
the physical characteristic of the first subject is sensed by the first sensor while the first subject is on the stationary apparatus.
69. The method of claim 68, wherein:
the physical characteristic of the first subject is sensed by the first sensor while the first subject is sitting on the stationary apparatus.
70. The method of claim 68, wherein:
the physical characteristic of the first subject is sensed by the first sensor while the first subject is resting on the stationary apparatus.
71. The method of claim 68, wherein:
the physical characteristic of the first subject is sensed by the first sensor while the first subject is standing on the stationary apparatus.
72. The method of claim 1, wherein:
the first device is a first sensor;
the physical characteristic of the first subject is sensed by the first sensor;
the receiving of the first data includes a remote server receiving the first data from the first sensor through the Internet; and
the method further comprises the remote server determining, based on the first data and based on the second data, an environmental condition of the first subject and of the second subject to alter.
73. The method of claim 72, wherein:
the environmental condition is the temperature of a room occupied by the first subject and by the second subject.
74. The method of claim 73, wherein:
the device is a software application operating on a computer; and
the computer has a touch screen input device.
75. The method of claim 73, wherein:
the first sensor is formed in a stationary apparatus; and
the physical characteristic of the first subject is sensed by the first sensor while the first subject is on the stationary apparatus.
76. The method of claim 73, wherein:
the first sensor is a wireless sensor; and
the remote server receiving of the first data from the first sensor through the Internet includes the remote server receiving the first data from the first sensor through a wireless connection between the first sensor and remote server.
77. The method of claim 76, wherein:
the wireless connection operates in the 2.4 GHz industrial, scientific and medical (ISM) frequency band.
78. The method of claim 1, wherein:
the first device is a first sensor;
the physical characteristic of the first subject is sensed by the first sensor;
the receiving of the first data includes a remote server receiving the first data from the first sensor through the Internet;
the first sensor is a first portable wireless sensor;
the first sensor is configured to wirelessly connect with a cellular telephone through a wireless connection;
the cellular telephone is configured to wirelessly connect to the Internet through a wireless cellular connection;
the remote server receiving of the first data from the first sensor through the Internet includes the remote server receiving the first data from the first sensor through the wireless connection between the first sensor and the cellular telephone and through the wireless cellular connection of the cellular telephone to the Internet; and
the first portable wireless sensor includes a subject perspiration sensor.
79. The method of claim 78, wherein:
the wireless connection operates in the 2.4 GHz industrial, scientific and medical (ISM) frequency band.
80. The method of claim 1, wherein:
the first device is a first sensor;
the physical characteristic of the first subject is sensed by the first sensor;
the receiving of the first data includes a remote server receiving the first data from the first sensor through the Internet; and
the determining of the evaluation includes the remote server determining, based on the first data and based on the second data, which of multiple options to provide to the first subject.
81. The method of claim 80, wherein:
the device is a software application operating on a cellular telephone; and
the cellular telephone has a touch screen input device.

82. The method of claim 80, wherein:
the first sensor is a first portable wireless sensor;
the first sensor is configured to wirelessly connect with a cellular telephone through a wireless connection;
the cellular telephone is configured to wirelessly connect to the Internet through a wireless cellular connection; and
the remote server receiving of the first data from the first sensor through the Internet includes the remote server receiving the first data from the first sensor through the wireless connection between the first sensor and the cellular telephone and through the wireless cellular connection of the cellular telephone to the Internet.

83. The method of claim 82, wherein:
the wireless connection operates in the 2.4 GHz industrial, scientific and medical (ISM) frequency band.

84. The method of claim 82, wherein:
the first portable wireless sensor includes a subject motion sensor.

85. The method of claim 82, wherein:
the first portable wireless sensor includes a subject acceleration sensor.

86. The method of claim 80, wherein:
the first sensor is physically connected to a cellular telephone;
the cellular telephone is configured to wirelessly connect to the Internet over a wireless cellular connection; and
the remote server receiving of the first data from the first sensor through the Internet includes the remote server receiving the first data from the first sensor over the wireless cellular connection of the cellular telephone to the Internet.

87. The method of claim 86, wherein:
the first sensor is a subject motion sensor.

88. The method of claim 86, wherein:
the first sensor is a subject acceleration sensor.

89. The method of claim 80, wherein:
the first sensor is formed in a stationary apparatus; and
the physical characteristic of the first subject is sensed by the first sensor while the first subject is on the stationary apparatus.

90. The method of claim 1, wherein:
the first device is a first sensor;
the physical characteristic of the first subject is sensed by the first sensor;
the receiving of the first data includes a remote server receiving the first data from the first sensor through the Internet; and
the determining of the evaluation includes the remote server determining, based on the first data and based on the second data, to provide multiple options to the first subject for the first subject to select from and to the second subject for the second subject to select from.

91. The method of claim 90, wherein:
the device is a software application operating on a cellular telephone; and
the cellular telephone has a touch screen input device.

92. The method of claim 90, wherein:
the first sensor is a first portable wireless sensor;
the first sensor is configured to wirelessly connect with a cellular telephone through a wireless connection;
the cellular telephone is configured to wirelessly connect to the Internet through a wireless cellular connection; and
the remote server receiving of the first data from the first sensor through the Internet includes the remote server receiving the first data from the first sensor through the wireless connection between the first sensor and the cellular telephone and through the wireless cellular connection of the cellular telephone to the Internet.

93. The method of claim 92, wherein:
the wireless connection operates in the 2.4 GHz industrial, scientific and medical (ISM) frequency band.

94. The method of claim 92, wherein:
the first portable wireless sensor includes a subject motion sensor.

95. The method of claim 92, wherein:
the first portable wireless sensor includes a subject acceleration sensor.

96. The method of claim 90, wherein:
the first sensor is physically connected to a cellular telephone;
the cellular telephone is configured to wirelessly connect to the Internet over a wireless cellular connection; and
the remote server receiving of the first data from the first sensor through the Internet includes the remote server receiving the first data from the first sensor over the wireless cellular connection of the cellular telephone to the Internet.

97. The method of claim 96, wherein:
the first sensor is a subject motion sensor.

98. The method of claim 96, wherein:
the first sensor is a subject acceleration sensor.

99. The method of claim 90, wherein:
the first sensor is formed in a stationary apparatus; and
the physical characteristic of the first subject is sensed by the first sensor while the first subject is on the stationary apparatus.

* * * * *

US006701271C2

(12) INTER PARTES REEXAMINATION CERTIFICATE (1254th)
United States Patent
Willner et al.

(10) Number: US 6,701,271 C2
(45) Certificate Issued: Mar. 31, 2016

(54) METHOD AND APPARATUS FOR USING PHYSICAL CHARACTERISTIC DATA COLLECTED FROM TWO OR MORE SUBJECTS

(75) Inventors: Barry E. Willner, Briarcliff Manor, NY (US); Edith H. Stern, Yorktown Heights, NY (US); David P. Greene, Ossining, NY (US); Philip Shi-lung Yu, Chappaqua, NY (US)

(73) Assignee: ICON HEALTH & FITNESS, INC.

Reexamination Request:
No. 95/002,337, Sep. 14, 2012

Reexamination Certificate for:
Patent No.: 6,701,271
Issued: Mar. 2, 2004
Appl. No.: 09/859,827
Filed: May 17, 2001

Reexamination Certificate C1 6,701,271 issued Nov. 5, 2015

(51) Int. Cl.
*G06F 15/00* (2006.01)
*G01D 1/00* (2006.01)
*A61B 5/00* (2006.01)
*G06F 19/00* (2011.01)
*G09B 23/28* (2006.01)

(52) U.S. Cl.
CPC ............ *A61B 5/0002* (2013.01); *G06F 19/322* (2013.01); *G06F 19/3418* (2013.01); *G06F 19/3487* (2013.01); *G09B 23/28* (2013.01)

(58) Field of Classification Search
None
See application file for complete search history.

(56) References Cited

To view the complete listing of prior art documents cited during the proceeding for Reexamination Control Number 95/002,337, please refer to the USPTO's public Patent Application Information Retrieval (PAIR) system under the Display References tab.

*Primary Examiner* — Minh T Nguyen

(57) ABSTRACT

A system, method, apparatus, and computer program code for using physical characteristic information obtained from two or more subjects to help evaluate subjects or to determine a course of action to take with the subjects includes receiving data indicative of one or more physical characteristics from two or more subjects, determining an evaluation of the data, and providing a notification to a device of the evaluation. A physical characteristic of a subject might be or include the subject's heart rate, blood pressure, blood sugar level, posture, temperature, respiration rate, facial response or position, weight, height, galvanic skin response, pheromone emission, brain wave pattern or rhythm, odor, motion, etc., or a change in any one or more of them.

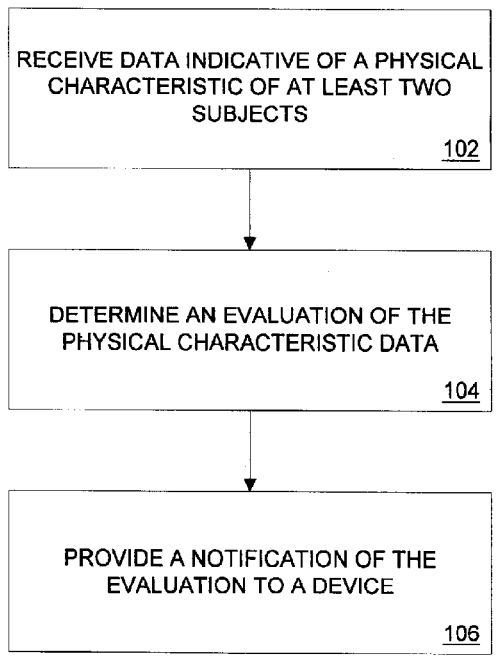

INTER PARTES REEXAMINATION CERTIFICATE

THE PATENT IS HEREBY AMENDED AS INDICATED BELOW.

AS A RESULT OF REEXAMINATION, IT HAS BEEN DETERMINED THAT:

The patentability of claim 15 is confirmed.

Claims 1-14 and 16-41 are cancelled.

\* \* \* \* \*